US00PP08976P

United States Patent [19]

Button

[11] Patent Number: Plant 8,976

[45] Date of Patent: Nov. 8, 1994

[54] AGLAONEMA PLANT NAMED MARY ANN

[75] Inventor: Richard J. Button, Miami, Fla.

[73] Assignee: Sunshine Foliage World, Zolfo Springs, Fla.

[21] Appl. No.: 174,052

[22] Filed: Dec. 28, 1993

[51] Int. Cl.[5] ..... A01H 5/00
[52] U.S. Cl. ..... Plt./88.1
[58] Field of Search ..... Plt. 88.1

*Primary Examiner*—James R. Feyrer
*Attorney, Agent, or Firm*—Foley & Lardner

[57] ABSTRACT

An Aglaonema plant named Mary Ann characterized by its bicolor leaves having a dark green background and lighter silvery green irregular base extending from the midrib to near the edge of the leaf, and by its branched, dense habit, and rapid growth.

1 Drawing Sheet

The present invention comprises a new and distinct cultivar of Aglaonema, botanically known as *Aglaonema hybrida,* and referred to by the cultivar name Mary Ann.

The new cultivar is a product of a planned breeding program carried out by the inventor Richard J. Button in Miami, Fla. The new cultivar is a product of a cross of unknown parentage.

The cultivar was discovered and selected from the progeny of the cross by the inventor in Miami, Fla. Asexual propagation by division first carried out by the inventor in Miami, Fla. and later carried out in Zolfo Springs, Fla. was used to increase the number of plants for evaluation and has demonstrated the stability of the characteristics of the new cultivar from generation to generation.

The following observations, measurements and values describe plants grown in Zolfo Springs, Fla. under shadehouse conditions which closely approximate those generally used in horticultural practice.

The following traits have been repeatedly observed to be characteristics which in combination distinguish Mary Ann from other Aglaonema of the same general type, for example, the commercially well known cultivar Maria.

1. The leaves of Mary Ann are larger, wider and have more silver markings than those of Maria.

2. The leaves, petioles, and stems of Mary Ann are lighter green than those of Maria.

3. Mary Ann has more branches than Maria.

4. The habit of Mary Ann is taller and more spreading than Maria.

5. Plants of Mary Ann grow to a marketable size from fewer cuttings in approximately 15% less time than Maria.

All color references are to The Royal Horticultural Society Colour Chart. Colors may vary somewhat depending on horticultural practices such as light level and fertilization rate, among others, without, however any variance in genotype.

The color photographic drawing comprises a top perspective view of Mary Ann.

The photograph is of a plant of Mary Ann grown in a 20.3 cm pot approximately 52 weeks after planting a single 4 leaf cutting, grown under appropriate growing conditions. Colors are as accurate as possible with color illustrations of this type.

Origin: Seedling selected from a cross of unknown parentage.

Classification: *Aglaonema hybrida,* cv, Mary Ann.

Propagation: Asexual propagation either by division or tissue culture.

Plant: When a 4 leaf cutting is grown in a 20.3 cm pot for 52 weeks under appropriate growing conditions, Mary Ann is approximately 11.5 cm to 17.0 cm in height, measured from the soil surface to the junction of the petioles of the last two (2) unrolled leaves, and approximately 54 cm to 59 cm in width.

(A) *Stem.*—(1) Growth pattern: The stem is erect in growth and is approximately 1.7 cm to 1.9 cm in diameter 5 cm above the soil surface. Internode distance is approximately 1.0 cm to 1.6 cm, 3 cm above the soil. (2) Color: The stem color is closest to but greener than 137C.

(B) *Petiole.*—The following information is based on the 4th expanded leaf from the apex. (1) Growth pattern: The petiole has fleshy edges, referred to as wings, extending from the midrib. The wings are approximately 5 mm to 6 mm wide one-half the distance from the petiole base to the wing apex. The wings extend from the base of the petiole to within approximately 1.8 cm to 2.7 cm of the base of the leaf. The apex of the wings is unevenly rounded and often torn. The petiole follows the stem axis but diverges from the axis approximately 1.5 cm to 2.5 cm from the leaf base, forming a horizontal distance from the edge of the stem to the leaf base of approximately 3.0 cm to 3.7 cm. (2) Dimensions: The petiole is straight from its base to approximately the end of the wing, and often curved from approximately the end of the wing to the base of the leaf. The petiole is approximately 6 mm in diameter one-half the distance between the top of the wing and the base of the leaf. The petiole is approximately 11.5 cm to 14.0 cm in length. (3) Color: The petiole is closest to 137B but darker and greener. The petiole wings are closest to 137A but darker and greener.

(C) *Leaf.*—(1) Growth pattern: The leaf is ovate with an acuminate apex and a cordate base. The margin is entire. The leaf is asymmetric with the side of the leaf unrolling first having less surface area than the side unrolling last. The leaf is oriented parallel to the stem axis at the time of full unrolling, changing to approximately 40 degrees above perpendicular to the stem axis as more leaves unroll above it. The midrib is straight over two-thirds the length of the leaf, and curved somewhat downward near the leaf tip. The leaf blade is flat from the midrib to the margin, and somewhat wavy along the margin. (2) Dimensions: For the pot size and growing time indicated, the largest leaves are approximately 25 cm to 27.5 cm long and approximately 8.0 cm to 10.3 cm wide. Average sized leaves are approximately 20 cm to 23.4 cm long and approximately 6.5 cm to 7.2 cm wide. The leaf is moderately thick. (3) Midrib: The midrib is thick and prominent, recessed on the adaxial leaf surface and protruding from the abaxial surface. The adaxial leaf midrib is 138A when new, and closest to 137A on older leaves, but darker and greener. The abaxial leaf midrib is 146D on both new and old leaves. (4) Primary veins: The primary veins are sunken into the upper surface and protrude slightly from the underside. The primary veins are 146A in color. (5) Color and pattern: The leaf is bicolor on the adaxial surface, with a dark green background and lighter silvery green irregular bars extending from the midrib to near the edge of the leaf. The background color of new leaves is 137A-138A, with the lighter irregular areas being greener than but closest to 139D. Older leaves have a background color closest to 137A but darker and greener, with the lighter irregular areas being 138B-C. The abaxial surface of both new and old leaves is 146C-D. (6) Axillary breaks: There are approximately 12 to 15 axillary breaks with at least one leaf expanded. Leaves will show true color and pattern by the first leaf. (7) Inflorescence: Typical of Aglaonema and does not have commercial significance.

(D) *Roots.*—Thick white roots with fine laterals.

General observation: Aglaonema Mary Ann has bicolor leaves marked with silver-green on a dark green background. The plant habit is branched, and dense. The plant grows rapidly, attaining a marketable size from fewer cuttings in less time than the closest commercial comparison, Aglaonema Maria. These combined characteristics make Mary Ann a unique new cultivar.

I claim:

1. A new and distinct cultivar of Aglaonema plant named Mary Ann, as illustrated and described.

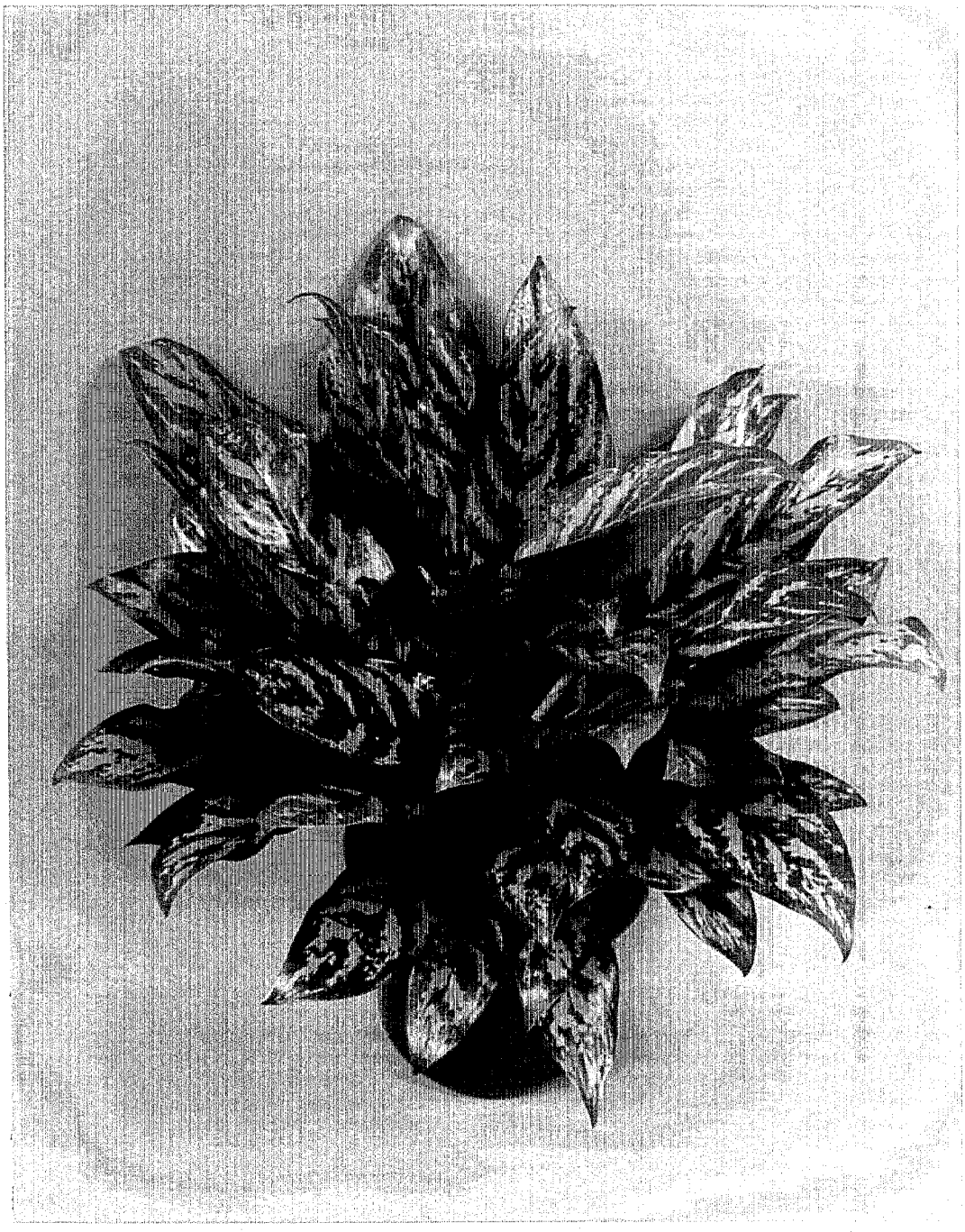

* * * * *